(12) United States Patent
Reimer

(10) Patent No.: US 11,039,743 B2
(45) Date of Patent: Jun. 22, 2021

(54) MEASUREMENT SYSTEM AND METHOD FOR ESTABLISHING THE REFRACTION OF AN EYE, THE RADIUS OF CURVATURE OF THE CORNEA OR THE INTERNAL PRESSURE OF AN EYE

(71) Applicant: Carl Zeiss Meditec AG, Jena (DE)

(72) Inventor: Peter Reimer, Ellwangen (DE)

(73) Assignee: CARL ZEISS MEDITEC AG, Jena (DE)

( * ) Notice: Subject to any disclaimer, the term of this patent is extended or adjusted under 35 U.S.C. 154(b) by 310 days.

(21) Appl. No.: 16/113,104

(22) Filed: Aug. 27, 2018

(65) Prior Publication Data

US 2018/0360309 A1    Dec. 20, 2018

Related U.S. Application Data

(62) Division of application No. 13/022,713, filed on Feb. 8, 2011, now Pat. No. 10,080,493.

(Continued)

(30) Foreign Application Priority Data

Feb. 12, 2010   (DE) .................... 10 2010 008 146.9

(51) Int. Cl.
*A61B 3/107*    (2006.01)
*A61B 3/103*    (2006.01)
(Continued)

(52) U.S. Cl.
CPC .............. *A61B 3/107* (2013.01); *A61B 3/103* (2013.01); *A61B 3/165* (2013.01); *A61F 9/007* (2013.01)

(58) Field of Classification Search
CPC ......... A61B 3/107; A61B 3/103; A61B 3/165; A61F 9/007
(Continued)

(56) References Cited

U.S. PATENT DOCUMENTS 3,996,935 A   12/1976 Banko
4,373,787 A    2/1983 Crane et al.
(Continued)

FOREIGN PATENT DOCUMENTS

DE      19702335      8/1998
EP       0563604     10/1993
(Continued)

OTHER PUBLICATIONS

H.D. Crane, et al., "Accurate three-dimensional eyetracker", Applied Optics vol. 17, No. 5, Mar. 1, 1978.
(Continued)

*Primary Examiner* — James C. Jones
(74) *Attorney, Agent, or Firm* — Nixon Peabody LLP; Jeffrey L. Costellia

(57) ABSTRACT

A method for establishing the refraction of an eye (9) by means of a refractometer (3) is provided, in which the current visual axis (S) of the eye (9) is established before establishing the refraction, the refractometer (3) is aligned with respect to the visual axis (S) of the eye (9) and the refraction is established after the alignment. The visual axis (S) of the eye (9) is established on the basis of the position of a Purkinje image of at least one light source (41, 50) used to illuminate the eye and a relationship between the position of the Purkinje image and the visual axis (S).

4 Claims, 4 Drawing Sheets

Related U.S. Application Data

(60) Provisional application No. 61/303,750, filed on Feb. 12, 2010.

(51) Int. Cl.
*A61B 3/16* (2006.01)
*A61F 9/007* (2006.01)

(58) Field of Classification Search
USPC .......................................................... 351/206
See application file for complete search history.

(56) References Cited

U.S. PATENT DOCUMENTS

| | | | |
|---|---|---|---|
| 4,443,075 A | 4/1984 | Crane | |
| 4,597,648 A | 7/1986 | Feldon et al. | |
| 4,812,033 A | 3/1989 | Ishikawa | |
| 5,090,797 A | 2/1992 | Cleveland | |
| 5,231,674 A | 7/1993 | Cleveland et al. | |
| 5,463,430 A | 10/1995 | Isogai et al. | |
| 5,474,548 A | 12/1995 | Knopp et al. | |
| 5,523,808 A | 6/1996 | Kohayakawa | |
| 5,563,670 A | 10/1996 | Tenmyo | |
| 5,570,157 A | 10/1996 | Konishi | |
| 5,585,873 A | 12/1996 | Shalon et al. | |
| 5,712,684 A | 1/1998 | Inoue et al. | |
| 5,848,175 A | 12/1998 | Akashi | |
| 5,865,742 A | 2/1999 | Massie | |
| 6,035,054 A | 3/2000 | Odaka et al. | |
| 6,036,316 A | 3/2000 | Arita | |
| 6,120,460 A | 9/2000 | Abreu | |
| 6,236,502 B1 | 5/2001 | Kitajima | |
| 6,299,307 B1 | 10/2001 | Oltean et al. | |
| 6,409,345 B1 | 6/2002 | Molebny et al. | |
| 6,659,611 B2 | 12/2003 | Amir et al. | |
| 2002/0049389 A1 | 4/2002 | Abreu | |
| 2002/0159031 A1 | 10/2002 | Kanngiesser | |
| 2003/0025877 A1 | 2/2003 | Yancey et al. | |
| 2003/0139736 A1 | 12/2003 | Sander | |
| 2005/0057723 A1 | 3/2005 | Wakil et al. | |
| 2006/0247659 A1 | 11/2006 | Moeller et al. | |
| 2008/0114283 A1 | 5/2008 | Mattson et al. | |
| 2008/0198329 A1 | 8/2008 | Gaida | |
| 2009/0030299 A1 | 1/2009 | Naito et al. | |
| 2009/0163898 A1 | 6/2009 | Gertner et al. | |
| 2014/0063456 A1* | 3/2014 | Zhou | A61B 3/132 351/206 |

FOREIGN PATENT DOCUMENTS

| | | |
|---|---|---|
| EP | 1338238 | 8/2003 |
| GB | 830 663 | 3/1960 |

OTHER PUBLICATIONS

Office Action in German Application No. DE-102010008146.9 dated Jan. 22, 2021; 10 pgs.

* cited by examiner

MEASUREMENT SYSTEM AND METHOD FOR ESTABLISHING THE REFRACTION OF AN EYE, THE RADIUS OF CURVATURE OF THE CORNEA OR THE INTERNAL PRESSURE OF AN EYE

CROSS-REFERENCE TO RELATED APPLICATIONS

This application claims priority under 35 USC 119 to German Patent Application No. 10 2010 008 146.9 filed on Feb. 12, 2010 and U.S. Provisional Patent Appl. No. 61/303,750 filed on Feb. 12, 2010, the entire disclosure of which is incorporated herein by reference.

BACKGROUND OF THE INVENTION

1. Field of the Invention

The present invention relates to a measurement system and a method for establishing the radius of curvature of the cornea, the refraction of an eye or the internal pressure of the eye. Additionally, the invention relates to a method and a system for adjusting the internal eye pressure.

2. Description of the Related Art

Establishing the refraction of the eye during surgery, i.e. intraoperatively, is of importance in a number of types of eye surgery. Examples thereof include the working of the corneal surface by means of laser beams to correct defective vision and cataract operations, in which the lens of the eye is replaced by an artificial lens. Methods and a device for determining the refraction of an eye are for example described in EP 0 563 604 A1 and EP 1 338 238 A2.

Irrespective of which method is used to establish the refraction, a problem always remains in ensuring that the refraction is also determined on the visual axis of the eye. This axis is not readily visible on the eye and sometimes differs significantly from the optical axis of the eye. This problem can be avoided by offering the eye a fixing marking, onto which the gaze can be fixed. However, this requires an active action of the patient and is only possible in the case of so-called eye drop anesthetics, in which the patient retains the ability to fixate objects and move the eye, provided the eye was not fixed by the surgeon. By contrast, if the patient is under general anesthesia or the patient's eye was anesthetized in a retrobulbar fashion, i.e. the anesthetic was injected behind the eyeball, the patient can no longer actively move the eye and can no longer actively fixate the eye either. The alignment of the visual axis of the eye, the refraction of which should be measured, is then completely arbitrary with respect to the measurement arrangement. If the measurement cannot be guaranteed to be taken on the visual axis, the measurement result will be afflicted by smaller or larger errors. By way of example, this can be redressed by measuring the eye before the operation and applying corresponding markings onto the eye of the patient. Such markings are used particularly with regard to the axis alignment of toric intraocular lenses within the scope of a cataract operation.

DE 197 02 335 has disclosed a device with a pulsed laser, which is suitable for corneal ablation. The eye is irradiated with infrared beams for beam tracking. A camera records images, generated by the infrared beams, of the eye, more particularly of the pupil, in the form of a light/dark contrast. A computer connected to the camera then establishes e.g. the centroid of the dark field, i.e. of the pupil, or the edge of the pupil, and so the eye movement could be established independently of the current pupil diameter. Although this can establish the position of the eye, it cannot establish the visual axis.

U.S. Pat. No. 6,299,307 B1 describes an eye-tracking device for laser surgery, in which the interface between the white sclera and the colored iris is established for determining the position of the eye. However, the visual axis cannot readily be calculated therefrom. Furthermore, this document explains that Purkinje images can be used to establish the eye position. However, it notes that the optical quality of the eye deteriorates temporarily during eye surgery, and so the Purkinje images go out of focus and this makes a precise determination of the eye position very difficult.

US 2006/0247659 A1 describes a surgical microscope system and a method for performing eye surgery. The system comprises an eye tracker, which analyzes images of the eye in order to establish the inner and outer boundary of the iris, the sclera and the eyelids. Image-processing software then establishes the largest connected dark region, which in practice corresponds to the pupil. The eye-tracking is then undertaken by determining the geometric center of the largest connected region. This method does not allow the visual axis to be determined.

U.S. Pat. No. 5,474,548 describes a method for establishing an unambiguous, machine-independent reference system for the eye. This method can be used in particular within the scope of eye surgery. It allows the alignment of the visual axis of the patient with regard to the optical axis of an ophthalmologic instrument, which is used for laser surgery or for diagnostic measurements. The method comprises moving the eye in the lateral direction until the images of a first and a second reference marking, which are located along the optical axis of the ophthalmologic instrument at different distances from the eye, align. During the treatment, the patient fixates the offered markings. This does not therefore allow the determination of the visual axis when the patient is under general anesthesia or in the case of retrobulbar anesthesia.

A further difficulty in the intraoperative refraction measurement lies in the fact that the internal eye pressure of the eye currently undergoing surgery can deviate significantly from the natural internal eye pressure, for example as a result of the injection of viscoelastic substances into the anterior chamber of the eye (to prevent the eye from collapsing during surgery). This modified internal eye pressure can lead to a change in the radius of the cornea and hence to a wrong refraction measurement.

It is therefore an object of the present invention to provide a method and a measurement system for establishing the refraction of an eye, which method and measurement system more particularly are also suitable for measuring the refraction intraoperatively, when the patient is under general anesthesia or in the case of retrobulbar anesthesia.

It is a further object of the invention to provide an advantageous measurement system and an advantageous method for establishing the radius of curvature and/or the internal pressure of an eye, which, more particularly, can also be used within the scope of a method for the intraoperative measurement of the refraction of an eye.

An additional further object of the present invention is to provide a system and a method for adjusting the internal pressure of an eye.

SUMMARY OF THE INVENTION

In the method according to the invention for establishing the refraction of an eye by means of a refractometer, the current visual axis of the eye is established before establishing the refraction. The refractometer is then aligned with respect to the visual axis of the eye and the refraction is established after the alignment. In the method, the visual axis of the eye is established on the basis of at least one Purkinje image of a light source used to illuminate the eye and a relationship between the position of the Purkinje image and the visual axis. Here, the term "Purkinje image" should be understood as meaning a reflection on an eye structure. There are different Purkinje images that can be observed on the eye. The first Purkinje image is the reflection on the outer surface of the cornea, the second Purkinje image is the reflection on the inner surface of the cornea, the third Purkinje image is the reflection on the outer surface of the lens and the fourth Purkinje image is the reflection on the inner surface of the lens. The first Purkinje image, i.e. the reflection on the outer surface of the cornea, is particularly suited to carry out the method according to the invention. The relationship between the position of the Purkinje image and the visual axis can be established either by means of a reference measurement or by means of a mathematical model. The light source can, in particular, emit visible light and can be embodied as a primary light source, i.e. a luminous light source such as an incandescent lamp or a luminescence emitter, or as a secondary light source, i.e. a non-luminous light source such as the outlet end of an optical waveguide.

The invention is based on the recognition that the refractometer can be aligned with respect to the visual axis of the eye by simple means, even without the aid of the patient, namely by establishing the position of a Purkinje image, more particularly the reflection of the light source on the outside of the cornea, on the eye. This position is unambiguously related to the visual axis of the eye. This relationship can be calculated using a mathematical model or, preferably, can be established empirically by undertaking a reference measurement before establishing the visual axis, during which reference measurement the patient is able to move the eye. The position of the Purkinje images can be determined and stored for a number of viewing directions during this reference measurement. During surgery, when either the patient is under general anesthesia or the eye was anesthetized in retrobulbar fashion, the stored positions of the Purkinje images can then be drawn upon in order to establish the visual direction on the basis of a recorded Purkinje image. Establishing the relationship between the position of the Purkinje images and the visual direction of the eye by empirical means is advantageous because this also allows the specific conditions of the respective eye to be taken into account. Thus, the position of the visual axis of the eye typically deviates by an angle of approximately 5° from the optical axis of the eye. However, deviations between 3° and 8° are also known, and, in extreme cases, there can also be deviations of up to 10°. A mathematical model cannot readily take account of such a variation, and so establishing the relationship between the visual axis and the Purkinje image on the basis of the mathematical model is less precise than establishing it by empirical means.

Moreover, according to the invention, provision is made for a method for establishing the radius of curvature of the cornea and/or the internal pressure of an eye. In this method, the eye is illuminated by at least one light source. The radius of curvature and/or the internal pressure are or is established on the basis of a property of at least one Purkinje image of the light source(s) and a relationship between this property and the radius of curvature and/or the internal pressure. In particular, the property can be the size of the Purkinje image, i.e. the area that the Purkinje image takes up on the cornea. If there are at least two light sources, the property can also be the distance of the Purkinje images from one another on the cornea. Herein, the distance can more particularly be considered to be the distance between their centers. As the radius of curvature of the cornea increases, so does the size of the Purkinje image or the distance from one another of the Purkinje images from two light sources. This is due to the fact that the outside of the cornea forms a convex mirror, and the size of the images of a convex mirror decreases with the radius of curvature of the mirror and hence with the focal length of the mirror.

As in the method for establishing the refraction of an eye, use can be made of a primary or secondary light source as light source. In the case of a plurality of secondary light sources, the number of primary light sources can equal the number of secondary light sources. However, it is also possible to provide fewer primary light sources than secondary light sources, with in this case at least two secondary light sources then being fed together from one primary light source.

The relationship between the property of the at least one Purkinje image and the radius of curvature and/or the internal pressure can be set on the basis of a mathematical model or by a reference measurement at a normal radius of curvature and/or normal internal pressure. The reference measurement is once again advantageous because the normal radius of curvature and/or the normal internal pressure of an eye are or is subject to variation that is difficult to handle by means of a mathematical model.

The first Purkinje image, i.e. the reflection of the light source(s) on the outside of the cornea, is particularly suited to carry out the method for determining the radius of curvature of the cornea and/or the internal pressure of an eye.

More particularly, the aforementioned reference measurement can be used to establish the normal radius of curvature and/or the normal internal pressure of the eye. The deviations from this normal internal pressure and/or the normal radius of the cornea can then be determined on the basis of a mathematical model. Here, the internal pressure can be deduced from the radius of curvature of the cornea with the aid of a physiological model. However, the physiological model is unnecessary if there should merely be monitoring as to whether the internal pressure is higher or lower than normal. Detailed knowledge of the relationship between the radius of curvature and the internal pressure is not required in that case.

The method according to the invention can be used to adjust the internal pressure of an eye during eye surgery and, more particularly, to keep said internal pressure constant. The deviation of the internal pressure from a target value can be determined with the aid of the method according to the invention for establishing the radius of curvature and/or the internal pressure. The internal pressure of the eye can then be brought to the target value on the basis of the determined deviation, for example by means of a rinsing fluid or by Injecting a viscoelastic substance, the pressure of which can be adjusted. Reaching the target value then emerges from the fact that the eye attains the normal radius of curvature and/or the normal internal pressure.

The method according to the invention for establishing the radius of curvature and/or the internal pressure moreover can be used in the method according to the invention for establishing the refraction of an eye. Then the radius of curvature and/or the internal pressure of the eye are or is established before the refraction is established. Then the established radius of curvature and/or the established internal pressure can be taken into account in the refraction measurement. A further option offered by the combination of the methods according to the invention lies in bringing the internal eye pressure to the normal value for the refraction measurement, and so the measured refraction can be compared directly to a refraction measurement carried out on the eye in the normal state of the eye prior to the operation.

In all methods according to the invention, the light source can be implemented by the illumination apparatus of a surgical microscope. This is advantageous because eye surgery is generally carried out with the aid of surgical microscopes and hence there is no need for an additional light source for the refraction measurement and/or the measurement of the curvature of the cornea and/or of the internal eye pressure. The illumination apparatus of a surgical microscope for eye surgery moreover typically affords the possibility of a coaxial Illumination, in which two Illumination beam paths run, coaxially with respect to the stereoscopic observation beam paths, between the microscope objective and the eye. This affords the possibility of observing the Purkinje images of two light sources. If there additionally is oblique illumination, it is possible to observe the Purkinje images of three light sources.

A measurement system according to the invention for establishing the refraction of an eye is embodied to carry out the method according to the invention and comprises a refractometer with an optical axis, at least one light source for illuminating the eye, an electronic image-recording device for recording an electronic image of the eye, and an image-processing unit, connected to the image-recording device in order to receive the electronic image, comprising means for determining the position of at least one Purkinje image, of the at least one light source, on the cornea of the eye on the basis of the electronic image. Furthermore, the measurement system comprises an evaluation unit, connected to the image-processing unit in order to receive the position of the at least one Purkinje image and embodied to establish the visual axis of the eye on the basis of the position of the at least one Purkinje image and a relationship between the position of the at least one Purkinje image and the visual axis, and an adjustment unit, connected to the evaluation unit in order to receive the visual axis of the eye and connected to the refractometer in order to align the refractometer with respect to the received visual axis.

The measurement system designed to carry out the method according to the invention is particularly suited to Intraoperative use during eye surgery. Here, the patient need not be in a position to move the eye; said patient can therefore also be under general anesthesia or the eye can be anesthetized in a retrobulbar fashion.

Moreover, according to the invention, provision is also made for a measurement system for establishing the radius of curvature and/or the internal pressure of an eye. This measurement system comprises at least one light source for illuminating the eye, which light source can be either a primary or a secondary light source. Furthermore, the measurement system comprises an electronic image-recording device for recording an electronic image of the illuminated eye and an image-processing unit, connected to the image-recording device in order to receive the electronic image, comprising means for determining the position and/or the size of at least one Purkinje image, of the at least one light source, on the cornea of the eye on the basis of the received electronic image. Additionally, the measurement device comprises an evaluation unit, connected to the image-processing unit in order to receive the position and/or the size of the at least one Purkinje image, for establishing the radius of curvature and/or the internal pressure on the basis of the position and/or the size of the at least one Purkinje image and a relationship between the position and/or the size of the at least one Purkinje image and the radius of curvature and/or the internal pressure.

This measurement system has been adapted to carry out the method according to the invention for establishing the radius of curvature of the cornea and/or the Internal pressure of an eye, and therefore affords the possibility of implementing the advantages described with reference to this method.

In a further embodiment of the measurement system for establishing the radius of curvature and/or the internal pressure of an eye, there are at least two light sources. The image-processing unit then comprises means for determining the distance of the Purkinje images of the light sources from one another on the cornea, and the evaluation device is designed for establishing the radius of curvature and/or the internal pressure on the basis of the distance of the Purkinje images of the light sources from one another on the cornea and a relationship between the distance and the radius of curvature and/or the distance and the internal pressure. In particular, this case can be considered as a special case of establishing the radius of curvature and/or the internal pressure on the basis of the position of two Purkinje images.

More particularly, the measurement system according to the invention for establishing the radius of curvature and/or the internal pressure of the eye can be combined with a measurement system according to the invention for establishing the refraction of an eye. The combination affords the possibility of taking into account the radius of curvature of the cornea and/or the internal pressure of the eye when establishing the refraction.

Both the measurement system for establishing the refraction of an eye and the measurement system for establishing the radius of curvature of the cornea and/or the internal pressure of the eye can be equipped with a medical-optical observation instrument, more particularly with a surgical microscope, which comprises an illumination device. In this case, the at least one light source is realized by a light source of the illumination device of the medical-optical observation instrument. In particular, the medical-optical observation instrument can be equipped with a coaxial illumination, in which two illumination beam paths run between the objective of the observation instrument and the eye, coaxially with respect to the stereoscopic observation beam paths. This affords the possibility of illuminating the eye with at least two light sources in a simple fashion The image-processing unit and/or the evaluation unit can be available in the form of hardware or software in all described measurement systems and the image-recording devices can for example be digital cameras with a CCD chip or a CMOS chip.

Moreover, according to the invention, provision is made for a system for adjusting the internal pressure of an eye during surgery. This system comprises a measurement system according to the invention for establishing the radius of curvature of the cornea and/or the internal pressure of an eye, a fluid supply apparatus for supplying a fluid, for example a rinsing fluid or a viscoelastic substance, into the eye, an adjustment apparatus for adjusting the pressure of the supplied fluid, and a difference registering unit, connected to the evaluation device of the measurement system in order to receive the established radius of curvature and/or the established internal pressure and to the adjustment apparatus in order to output a correcting variable. The difference registering unit is designed to establish a deviation of the received radius of curvature and/or the received internal pressure from a target value and to calculate the correcting variable on the basis of the established deviation from the target value.

The system according to the invention for adjusting the radius of curvature and/or the internal pressure of an eye can be used to adjust the radius of curvature of the cornea and/or the internal pressure of the eye to a target value, or to maintain the latter. In particular, the normal radius of curvature and/or the normal internal pressure of the eye come into question as target value, and so the system according to the invention can be used to bring the radius of curvature and/or the internal pressure to the normal value during surgery, or keep it/them there. More particularly, if the system for adjusting the radius of curvature and/or the internal pressure of an eye is combined with a measurement system for establishing the refraction of an eye, it is possible to ensure that the refraction can be measured during surgery with a normal radius of curvature and/or a normal internal pressure of the eye.

The present invention offers the possibility of measuring properties of the eye, in a simple fashion and intraoperatively, on the basis of recording the at least one Purkinje image of a light source; these properties can be used within the scope of a refraction measurement in particular. Further features, properties and advantages of the present invention emerge from the following description of exemplary embodiments, with reference to the attached figures.

DETAILED DESCRIPTION OF THE PREFERRED EMBODIMENTS

Figure 1:
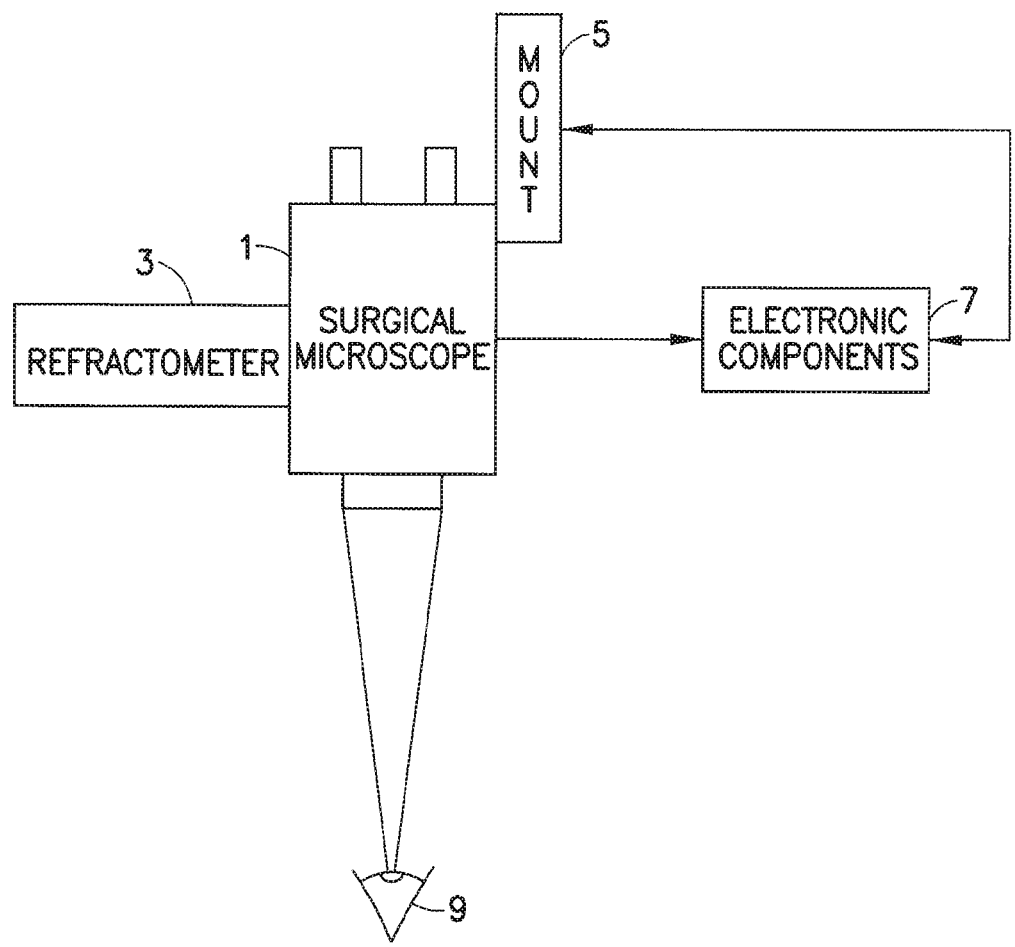
FIG. 1 shows a measurement system according to the invention, comprising a surgical microscope, for establishing the refraction of an eye.

A first aspect of the invention provides a measurement system for establishing the refraction of an eye. Such a measurement system has been illustrated schematically in FIG. 1. It comprises a surgical microscope 1, a refractometer 3 and a microscope mount 5, which is part of a stand (not illustrated) that together with the mount 5 provides three translational degrees of freedom and up to three rotational degrees of freedom. In this context, it should be noted that stands and mounts for opthalmological applications often only provide two rotational degrees of freedom. The stand in conjunction with the mount 5 thus allows arbitrary positioning and orienting of the surgical microscope 1.

The measurement system moreover comprises electronic components 7, which are used to establish the suitable alignment of the refractometer 3 with respect to the visual axis of that eye 9 whose refraction should be measured.

In the present exemplary embodiment, the refractometer 3 is fixedly coupled to the surgical microscope 1, and so the refractometer 3 can be aligned by suitably aligning the surgical microscope 1. To this end, the electronic components 7 are connected to the surgical microscope 1 for the purpose of receiving electronic signals and connected to the microscope mount 5 and possibly the stand (not illustrated) for the purpose of outputting electronic correcting signals.

Figure 2:
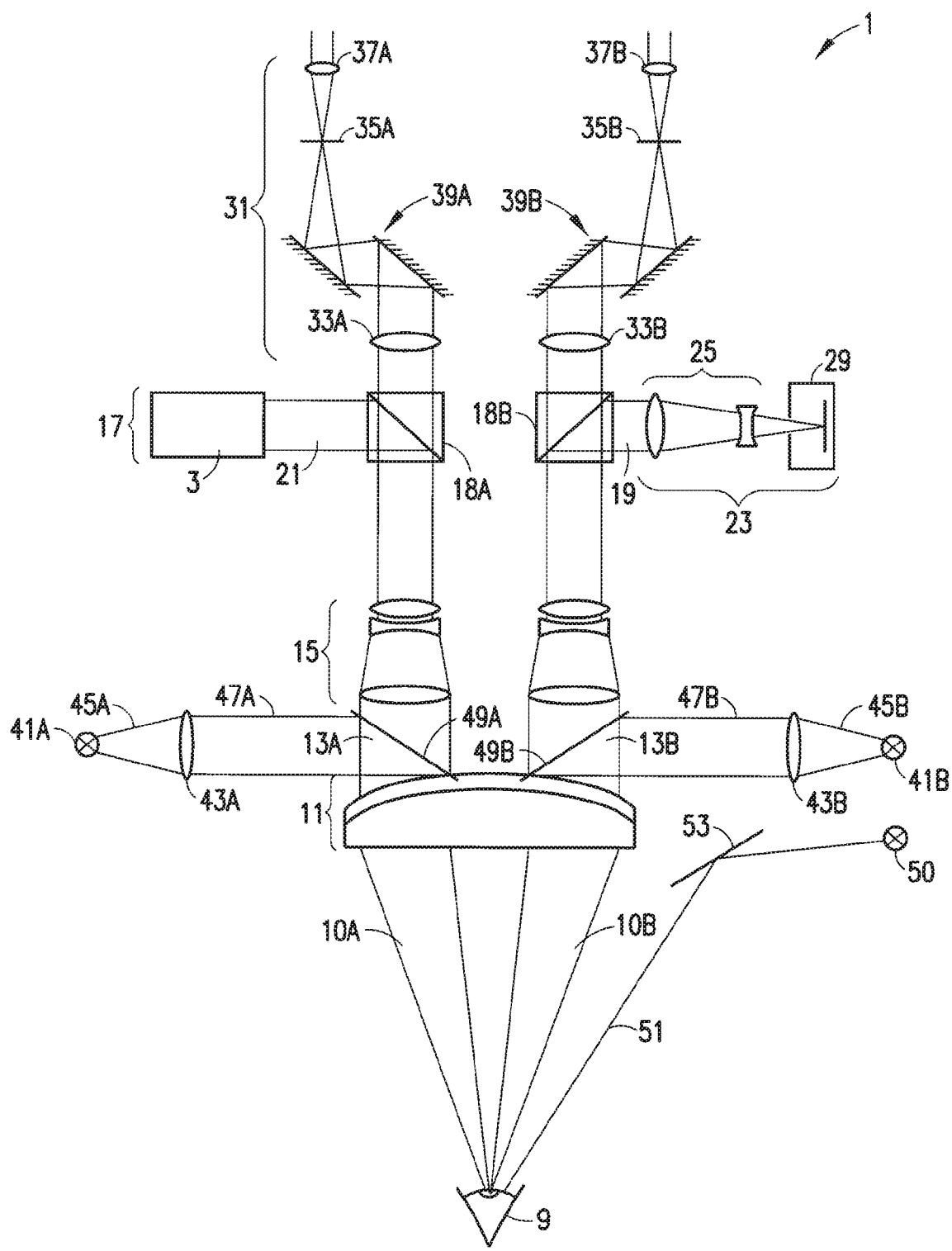
FIG. 2 shows the essential components of the surgical microscope from FIG. 1 in a schematic illustration.

The surgical microscope 1 of the measurement system from FIG. 1 is illustrated in detail in FIG. 2. The surgical microscope 1 comprises, as essential components, a main objective 11, which should face the eye 9 and which in the present exemplary embodiment is Illustrated as a cemented component that is made up of two partial lenses that have been cemented together. The observed region of the eye 9 is arranged in the focal plane of the objective 11, and so a divergent bundle of rays 10A, 10B emanating from the observed region of the eye 9 is imaged at infinity by the main objective 11, i.e. it is converted into a parallel bundle of rays 13 after passing through the main objective 11. In place of an individual objective lens, as is used in the present exemplary embodiment, it is also possible to make use of an objective-lens system comprising a plurality of individual lenses, for example a so-called varifocal lens, by means of which the working distance of the microscope, i.e. the distance between the focal plane and the objective-lens system, can be varied. The observed region of the eye 9 arranged in the focal plane is also imaged at infinity in such a varifocal system, and so there also is a parallel bundle of rays on the image side in the case of a varifocal lens.

A magnification changer 15 is arranged on the image side of the main objective 11 and it can be embodied either as a zoom system for a continuous change in the magnification factor as in the exemplary embodiment or as a so-called Galilean system for discretely changing the magnification factor. In the case of a zoom system, which comprises at least three lenses, the two object-side lenses can be displaced in order to vary the magnification factor. By contrast, in a Galilean system there are a plurality of fixed lens combinations that can alternately be introduced into the beam path. Both a zoom system and a Galilean changer convert a parallel bundle of rays on the object side into a parallel bundle of rays on the image side with a different bundle diameter. In the present exemplary embodiment, the magnification changer 15 is already part of the binocular beam path of the microscope, i.e. it has its own lens combination for each stereoscopic partial bundle of rays 13A, 13B in the surgical microscope.

On the image side, the magnification changer 15 is adjoined by an interface 17, by means of which external instruments can be connected to the surgical microscope 1. In the present exemplary embodiment, the interface 17 serves for decoupling a parallel bundle of rays 19 out of the beam path of the parallel stereoscopic partial bundle of rays 13B and for coupling and decoupling a parallel bundle of rays 21 into and out of the beam path of the parallel stereoscopic partial bundle of rays 13A. In the present exemplary embodiment, the interface 17 comprises beam-splitter prisms 18A, 18B, which are arranged in the respective stereoscopic partial beam paths.

A camera-adapter combination 23 is arranged on the interface 17 of the surgical microscope 1 illustrated in FIG. 1; the combination comprises a camera adapter 25 and a camera 27 attached thereto with at least one electronic image sensor 29, for example with a CCD sensor or a CMOS sensor. The camera adapter 25 converts the parallel bundle of rays 19, decoupled from the beam path of the microscope 1 by means of the beamsplitter prism 18B, into a convergent bundle of rays and hence the observation object is imaged on the at least one electronic image sensor 29.

Moreover, the refractometer 3 is connected to the interface 17 in the present exemplary embodiment. For the purpose of a refraction measurement, light generated by the refractometer 3 is coupled into the partial beam path in the direction of the eye 9 via the beamsplitter prism 18A and is imaged on the retina of the eye 9 via the magnification changer 15 and the main objective 11. The light reflected by the retina is then fed back to the refractometer 3 in order to be analyzed via the main objective 11, the magnification changer 15 and the beamsplitter prism 18A. Any suitable method known from the prior art can be used for the analysis; a person skilled in the art can readily recognize this. By way of example, infrared light can be used as light for the refraction measurement.

Although the refractometer 3 in the present exemplary embodiment is connected to the interface 17 situated downstream of the magnification changer 15, it can, in principle, also be attached to other locations on the surgical microscope 1, where beamsplitters specifically provided for coupling and decoupling the light emanating from the refractometer and/or reflected from the retina can also be available. Such beamsplitters can, for example, be arranged between the main objective 11 and the magnification changer. Herein, there can in principle be both a central and a local position of the beamsplitters with respect to the main objective 11.

On the image side, a binocular tube 31 adjoins the interface 17. The former has two tube objectives 33A, 33B, which focus the respective parallel bundle of rays 13A, 13B in an intermediate-image plane 35, that is to say they image an observed region of the eye 9 on the respective Intermediate-image plane 35A, 35B. The intermediate images located on the intermediate-image planes 35A, 35B are finally in turn imaged at infinity by eyepiece lenses 37A, 37B, and so an observer, for example a treating medical practitioner or an assistant thereof, can observe the intermediate image with a relaxed eye. Furthermore, the distance between the two partial bundles of rays 13A, 13B is increased in the binocular tube by means of a system of mirrors or by means of prisms 39A, 39B in order to match said distance to the distance between the eyes of the observer.

The surgical microscope 1 moreover comprises an illumination device, which is illustrated schematically in FIG. 2 and, in particular, allows coaxial illumination. In the coaxial illumination, two partial illumination bundles of rays are coupled into the stereoscopic partial beam paths such that they are guided to the eye 9 in a coaxial fashion with respect to the beam paths of the partial observation bundles of rays 10A, 10B. In particular, such an illumination allows the observation of the lens by means of so-called red reflex, i.e. by means of light reflected by the retina of the eye. Such red-reflex illumination is of great importance, particularly during cataract operations. Moreover, such an illumination makes the pupil particularly visible, which can be advantageous when establishing the position of Purkinje images.

In the present exemplary embodiment, the coaxial illumination is illustrated by two light sources 41A, 41B and associated illumination optical systems 43A, 43B. The illumination optical systems, which are merely indicated as lenses in very schematic fashion in FIG. 2, convert Illumination bundles of rays 45A, 45B, which are divergent and emanate from the light sources 41A, 41B, into illumination bundles of rays 47A, 47B, which are in parallel and coupled into the stereoscopic partial observation beam paths in the direction of the eye 9 via beamsplitters 49A, 49B that are arranged between the main objective 11 and the magnification changer 15. Here, either primary or secondary light sources can be used as light sources 41A, 41B. Incandescent lamps, e.g. halogen lamps, or luminescence emitters, e.g. light-emitting diodes, are suitable as primary light sources. The outlet ends of optical waveguides or real images of light sources in particular can be used as secondary light sources. Here, the secondary light sources need not necessarily each be generated by an individual primary light source. Rather, it is also possible to feed the light from a single primary light source to two separate outlet ends of the optical waveguide, e.g. by means of a spliced optical waveguide, or to generate two images from a single primary light source by means of a suitable optical system.

In addition to the coaxial illumination, the present surgical microscope has a so-called oblique illumination, in which the illumination beam path runs at an angle to the optical axis of the main objective 11 and does not run coaxially with respect to the beam paths of the observation bundles of rays 10A, 10B. The oblique illumination is illustrated schematically in FIG. 2 by a light source 50, an illumination beam path 51 and a deflection mirror 53 for deflecting the illumination beam path 51 in the direction of the eye 9. The statement regarding the use of primary or secondary light sources made with respect to the light sources 41A, 41B analogously holds for the light source 50.

Although the illumination beam path 51 of the oblique illumination runs outside of the main objective 11 in FIG. 2, it often runs through the main objective 11 such that the deflection mirror 53 is arranged between the main objective 11 and the magnification changer 15 like the beamsplitters 49A, 49B. In order to avoid vignetting of the observation beam paths, the arrangement of the deflection mirror 53 for the oblique illumination is typically rotated about the optical axis of the main objective 11 by 90° with respect to the orientation of an imagined connecting line between the beamsplitter prisms 49A, 49B (i.e. the deflection mirror 53 would project from or project into the image plane in FIG. 2). Rather than being arranged between the main objective 11 and the magnification changer 15, the deflection mirror 53 can also be arranged between the main objective 11 and the eye 9. The oblique illumination typically serves as surrounding-medium illumination during cataract surgery, for example.

Figure 3:
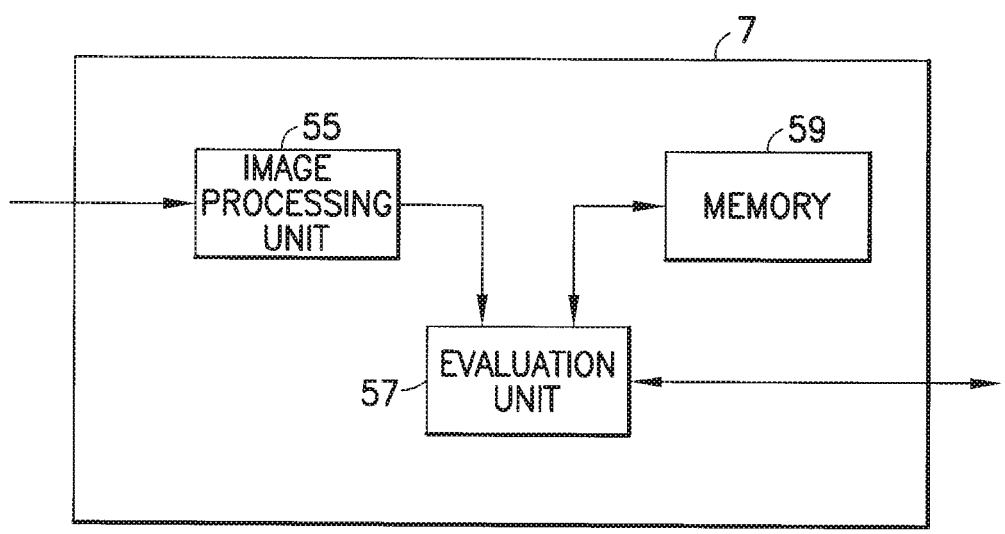
FIG. 3 shows the electronic components of the measurement system from FIG. 1 in the form of a block diagram.

In order to be able to undertake a more precise refraction measurement using the measurement system illustrated in FIG. 1, it is important that the refractometer 3 is aligned with respect to the visual axis of the eye 9. In the present exemplary embodiment, this is achieved by a suitable alignment of the surgical microscope 1. The electronic components 7 are used to establish the visual axis of the eye 9 and to align the surgical microscope 1 with the aid of the mount 5 and optionally with the aid of the stand. With reference to FIG. 3, said electronic components are explained in more detail in the following text.

Figure 4:
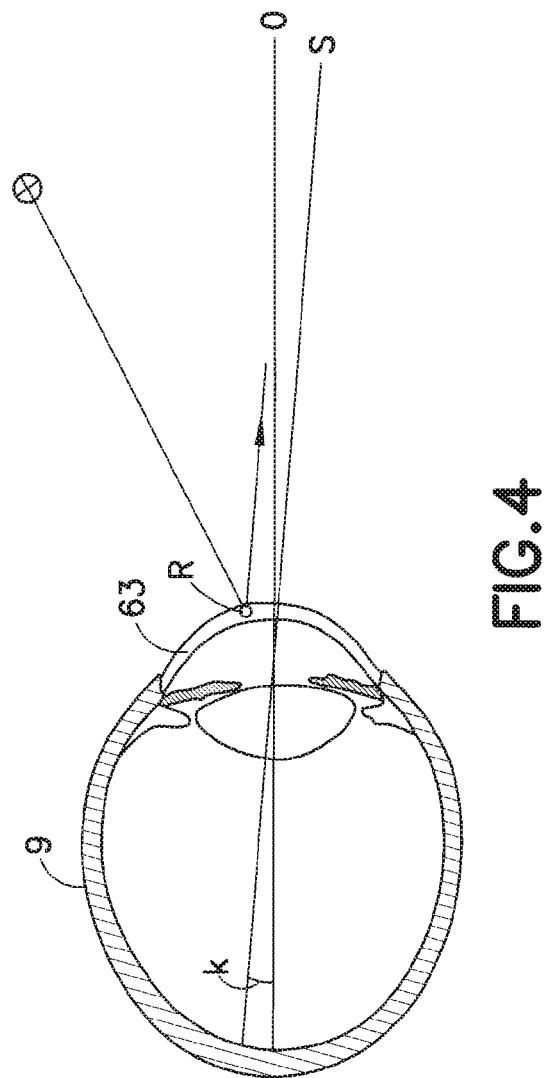
FIG. 4 shows a schematic illustration of an eye with visual axis, optical axis and the reflection of a beam path on the cornea.

The electronic components 7 of the measurement system for the refraction measurement comprise an image-processing unit 55, an evaluation unit 57 and random access memory (RAM) 59. The image-processing unit 55 is connected to the camera 27 in order to receive an electronic image of the eye 9, and it is designed for locating the first Purkinje images of the light sources of the surgical microscope 1 in the electronic image and for establishing the position of the Purkinje images on the cornea, for example with reference to the pupil boundary. In the present exemplary embodiment, use is made in particular of the first Purkinje images of the light source. These are generated by a reflection R of light from the light sources 41 on the outside of the cornea 63, as illustrated in FIG. 4. Moreover, the optical axis O of the eye and the visual axis S of the eye are indicated in FIG. 4. The visual axis S runs at an angle κ to the optical axis, wherein the angle lies in the range between 3° and 8°, and typically is approximately 5°. However, angles of up to 10° occur as well.

The evaluation device 57 is connected to the image-processing unit 55 in order to receive data that reproduces the position of the Purkinje images on the cornea. Furthermore, said evaluation device is connected to the memory 59, which stores a relationship between the position of the Purkinje images on the cornea, e.g. with reference to the boundary of the pupil, and that vector representing the direction of the visual axis of the eye. In principle, this relationship can be stored as a functional relationship, in which the orientation of the visual axis S is linked to the position of the Purkinje images on the cornea by means of a mathematical model. Here the angle κ is set to e.g. 5 degrees. However, provision can also be made for the option of entering a deviating value for the angle κ. However, another way was selected in the present exemplary embodiment. Here, the link is stored in the memory 59 in the form of a table. The table associates the respective position of the Purkinje images on the cornea with a plurality of orientations of the visual axis S. This table can be created during a reference measurement, during which the patient is able to follow a prescribed marking with his/her gaze. The associated Purkinje images are recorded for a plurality of positions of the marking and then are stored in the memory 59 in the form of the addressed table. The number of marking positions applied in the reference measurement depends on the accuracy with which the orientation of the visual axis S should subsequently be determined.

Compared to the use of a mathematical model, an advantage of the reference measurement is that the latter can be carried out individually on the eye for which the orientation of the visual axis should later be established intraoperatively. This allows physiological properties and peculiarities of the respective eye, more particularly the angle κ, to be automatically taken into account in the subsequently used reference. When a mathematical model is used, this cannot readily be taken into account, and so the reference measurement generally allows an increased accuracy when establishing the orientation of the visual axis compared to the use of the mathematical model.

The orientation of the visual axis S of the examined eye 9 is established on the basis of the electronic Image of the eye that was obtained Intraoperatively; this is brought about by the image-processing unit 55 establishing the position of the Purkinje images on the cornea, for example with respect to the edge of the pupil, and passing this position on to the evaluation unit 57. Here the reference system in which the measurement is undertaken preferably corresponds to the reference system during the reference measurement in order to avoid coordinate transformations. The evaluation unit 57 then establishes the current orientation of the visual axis S by a comparison between the position of the Purkinje images and the positions in the table, stored in the memory 59. The evaluation unit 57 then uses the orientation of the visual axis S established thus and information relating to the orientation of the surgical microscope 1 obtained from the mount device 5 and/or the stand to establish the required correcting variables for the mount 5 and/or the stand in order to match the orientation of the surgical microscope 1 to the orientation of the visual axis. The refraction measurement is subsequently carried out after the orientation of the microscope 1 has been matched to the orientation of the visual axis S. This ensures that the refraction measurement always takes place on the visual axis of the eye.

In principle, all available Purkinje images in the eye can be used to establish the orientation of the visual axis S. These are the first Purkinje images of the light sources, which represent the reflections on the outside of the cornea, the second Purkinje images, which represent the reflections on the inside of the cornea, the third Purkinje images, which represent the reflections on the outside of the lens, and the fourth Purkinje Images, which represent the reflections on the inside of the lens. Here, it is necessary to take into account the fact that the fourth Purkinje images are upside down due to the reflected light passing through the lens. As mentioned previously, use can in principle be made of the first, the second, the third or the fourth Purkinje images of the light sources for establishing the orientation of the visual axis. In principle, it is also possible to make use of a combination of various Purkinje images. Moreover, evaluating the Purkinje images of all light sources is unnecessary; in principle, it is enough to evaluate the Purkinje image of one of the utilized light sources.

Figure 5:
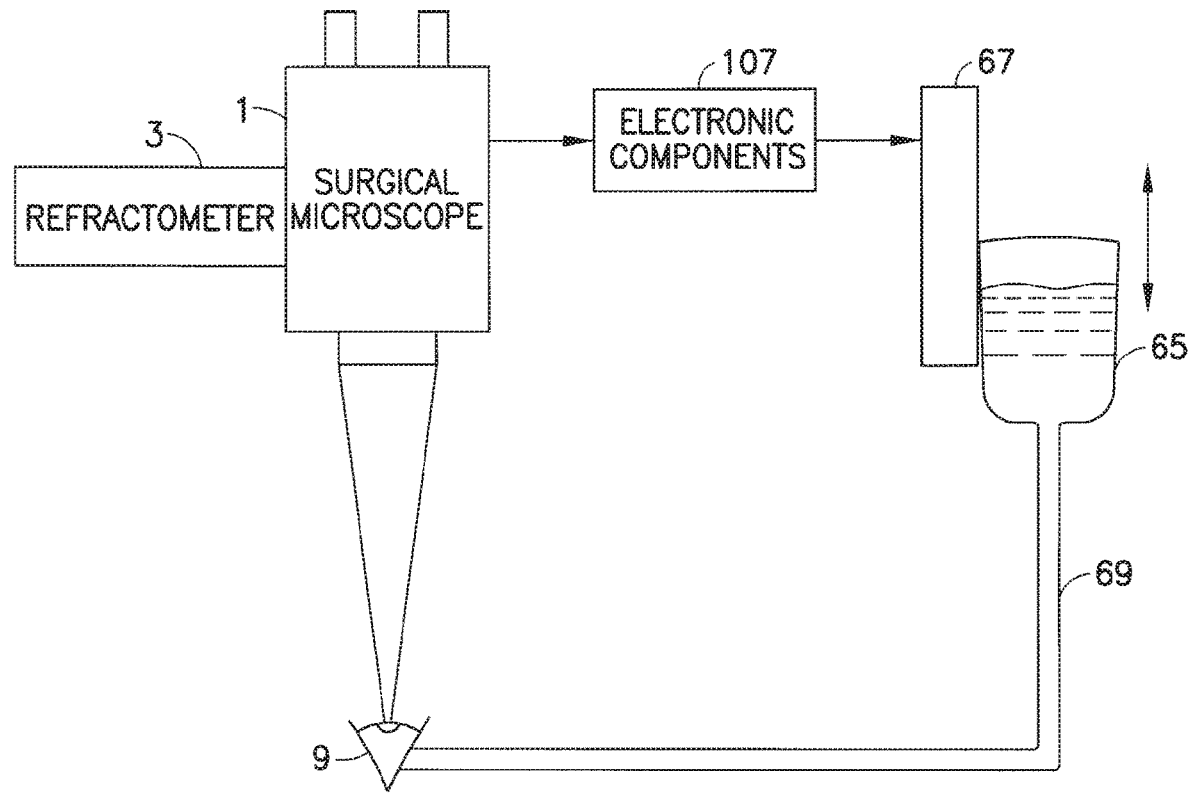
FIG. 5 shows a system for adjusting the radius of curvature and/or the internal pressure of an eye.

Moreover, according to the invention, provision is made for a measurement system for establishing the radius of curvature of the cornea and/or the internal pressure of the eye. Such a system can be used, in particular, for adjusting the radius of curvature and/or the internal pressure of the eye to a target value or for keeping it at a prescribed value. The measurement system for establishing the radius of curvature of the cornea and/or the internal pressure of the eye is therefore described below within the scope of a system for adjusting the radius of curvature of the cornea and/or the internal pressure of the eye. This system is illustrated in FIG. 5 in a very schematic fashion. It comprises a surgical microscope 1, as already described with reference to FIGS. 1 and 2. However, the refractometer 3 is not required in either the measurement system for establishing the radius of curvature of the cornea and/or the internal pressure of the eye, or in the system for adjusting the radius of curvature and/or the internal pressure. The system for adjusting the radius of curvature and/or the internal pressure furthermore comprises electronic components 107 and a bottle 65 with rinsing fluid for the eye 9, which bottle can be adjusted in terms of height above the eye 9 with the aid of a slide 67. The rinsing fluid is guided into the eye 9 during surgery by means of a tube 67. The height of the bottle can be used to adjust the rinsing-fluid pressure at the outlet end of the tube 67, i.e. the pressure of the rinsing fluid in the eye, in a suitable fashion. The bottle height to be set is established by the electronic components 107.

Figure 6:
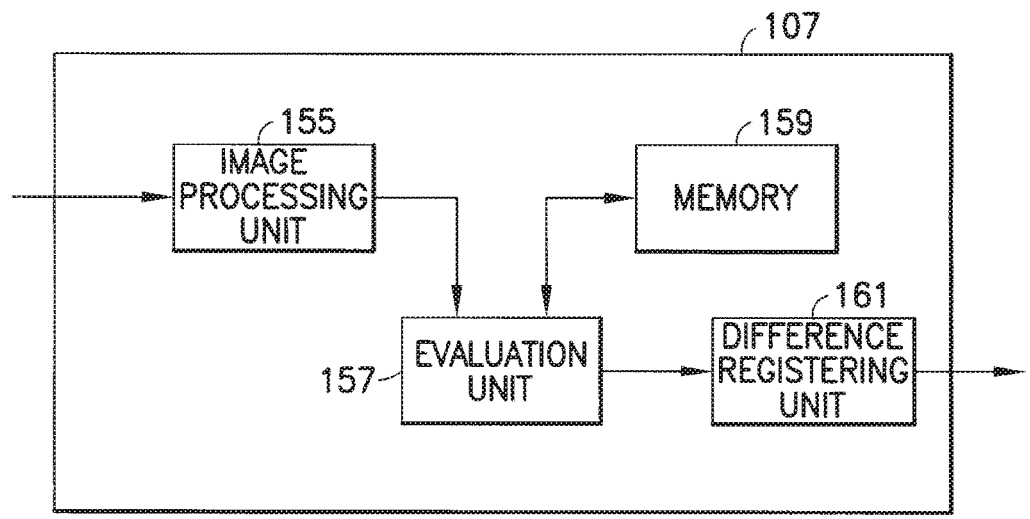
FIG. 6 shows the electronic components of the system from FIG. 4 in the form of a block diagram.

The electronic components 107 are illustrated in the form of a block diagram in FIG. 6. They comprise an image-processing unit 155, an evaluation unit 157, random access memory (RAM) 159 and a difference registering unit 161. The image-processing unit 155 is connected to the camera 27 of the surgical microscope 1 in order to receive an electronic image of the eye 9. It is designed to establish the size of the Purkinje images of the light sources from the received image. The cornea can be considered to be a convex mirror that generates a virtual image of the light sources. The size of this virtual image decreases with the size of the radius of curvature of a convex mirror. Hence, the radius of curvature of a convex mirror can be deduced from the size of the image. This is also possible in the case of the cornea The size of the Purkinje image of the light sources likewise allows conclusions to be drawn in respect of the internal pressure in the eye, since an increase in the internal pressure leads to an increase in the radius of curvature, and a decrease in the internal pressure leads to a decrease in the radius of curvature of the cornea.

The size of the Purkinje image of the light sources established in the image-processing unit 155 is transmitted to the evaluation unit 157, which is connected to the image-processing unit 155. There, the internal pressure of the eye 9 is determined in the present exemplary embodiment on the basis of the established size of the Purkinje image. This can be brought about on the basis of a mathematical model that links the radius of curvature of the eye with the internal eye pressure. The size of the Purkinje Images with respect to the cornea can then be used to establish the radius of curvature of the cornea, and this radius of curvature can in turn be used to establish the internal eye pressure. However, no mathematical model is used in the present exemplary embodiment; rather, a reference measurement is carried out before the eye surgery, during which reference measurement the normal internal pressure of the eye and the associated size of the Purkinje images are registered. Moreover, the internal pressure can be increased temporarily by exerting a pressure on the eye, and so a reference can also be established within the scope of the reference measurement for the behavior of the cornea when the internal pressure changes—and thus a reference can also be established for the change in size of the Purkinje images as a function of the internal pressure. The size of the Purkinje images of the light sources at normal internal eye pressure, registered during the reference measurement, can thus constitute e.g. a target value, which should be maintained in the eye during surgery. The relationship between the change in size in the Purkinje images and the internal pressure established during the reference measurement can be used to determine whether the internal pressure is too high or too low if the size of the Purkinje images deviates from the established reference size. The target value and the relationship between the change in size of the Purkinje images and the internal pressure are stored in the memory 159, which is likewise connected to the evaluation unit 157, and can be recalled during the operation. Then the evaluation unit 157 can compare the size of the Purkinje images of the light sources, established during the operation, with the size of the reference Purkinje images. If the Purkinje images of the light sources recorded during the operation deviate from the size of the reference Purkinje images at normal internal pressure, measures for correcting the internal pressure may optionally be initiated. When the size is determined it is advantageous if this occurs in the same reference system as in the reference measurement in order to avoid coordinate transformations.

In the difference registering unit 161, which is connected to the evaluation unit 157 in order to receive the established radius of curvature and/or the established internal pressure, a determined deviation in the size of the Purkinje images recorded during surgery from those Purkinje images recorded during the reference measurement establishes a correcting variable, which represents the height at which the rinsing-fluid bottle 65 should be set and should be output to the slide 67. This correcting variable is output to the slide 67 in order to set the rinsing-means pressure via the height of the bottle such that the normal eye pressure is set or the latter is maintained. This affords the possibility of maintaining the internal eye pressure at the normal value throughout an operation.

In the present exemplary embodiment, the size of the Purkinje images of the light sources, i.e. the area that the Purkinje images take up with respect to the cornea, has been used as an indicator for the curvature of the cornea and/or the internal eye pressure. If there are a plurality of light sources, as is the case in the present exemplary embodiment, the distance of the light sources from one another in the Purkinje image can also be used in place of the size of the light sources in order to establish the radius of curvature and/or the internal eye pressure. However, establishing the radius of curvature and/or the internal eye pressure on the basis of the size of the Purkinje image is advantageous because there merely needs to be one light source.

In the exemplary embodiment described with reference to FIGS. 5 and 6, the measurement device for establishing the radius of curvature of the cornea and/or the internal pressure of the eye is used to adjust the internal eye pressure to a target value. However, it is also possible merely to establish the radius of curvature and/or the internal eye pressure and to use the established radius of curvature and/or the established internal eye pressure in a measurement of the refraction of the eye. This is because the refraction of the eye depends on the internal eye pressure and on the radius of curvature of the cornea. Hence it is advantageous to combine the measurement device for establishing the radius of curvature of the cornea and/or the internal pressure of the eye with a measurement device for establishing the visual axis of the eye. This combination affords the possibility of either always carrying out the refraction measurement at normal internal eye pressure, and hence at a normal radius of curvature of the eye, or taking account of the established radius of curvature of the cornea and/or the established internal eye pressure in the refraction measurement. If the internal pressure should not be adjusted, the difference registering unit can also be dispensed with Overall, the invention offers the possibility of establishing, on the basis of recording the Purkinje images of the light sources of the surgical microscope, a plurality of eye parameters that are relevant during eye surgery. Although this was described using concrete exemplary embodiments, deviations from this are possible. Thus, the light sources do not necessarily need to be light sources from the surgical microscope. Instead, they could be additional light sources, which are used specifically for recording the Purkinje images. However, they can also be light sources from other instruments used during the operation. Likewise, it is not mandatory for the refractometer 3 to be integrated into the surgical microscope 1. There could just as well be an independent instrument, wherein in this case it is of course not the surgical microscope that is aligned with respect to the visual axis of the eye, but the refractometer. Furthermore, it is not mandatory to establish the radius of curvature of the cornea and/or the internal eye pressure by means of the recorded Purkinje images within the scope of the refraction measurement. Rather, there can be a keratoscope for establishing the radius of curvature of the cornea. It can also be advantageous to superimpose the results obtained by the measurement devices into the observation beam path of the surgical microscope in order to make them accessible to the treating medical practitioner. By way of example, if the internal eye pressure is not adjusted automatically, it may be advantageous for the established internal eye pressure to be mirrored into the observation image for the treating medical practitioner such that the latter can optionally take up countermeasures if the internal eye pressure and/or the radius of curvature of the cornea assume undesired values. Likewise, it is also possible for the position of the visual axis to be mirrored into the observation image, and so the treating medical practitioner can manually adjust the surgical microscope and/or the refractometer rather than there being an automatic adjustment thereof.

What is claimed is:

1. A measurement system for establishing an internal pressure of an eye, comprising:
   at least one light source for illuminating the eye;
   an electronic image-recording device for recording an electronic image of the illuminated eye;
   an image-processing unit connected to the image-recording device to receive the electronic image, the image-processing unit comprising means for determining a position and/or the size of at least one Purkinje image of the at least one light source on a cornea of the eye based on the received electronic image; and
   an evaluation device, connected to the image-processing unit to receive a position and/or a size of the at least one Purkinje image for establishing the internal pressure on a basis of the position and/or the size of the at least one Purkinje image and a relationship between the position and/or the size of the at least one Purkinje image and the internal pressure.

2. The measurement system of claim 1, where the at least one light source comprises at least two light sources and the image-processing unit comprises means for determining a distance of the Purkinje images of the at least two light sources from one another on the cornea and the evaluation device is designed for establishing the internal pressure based on the distance of the Purkinje images of the at least two light sources from one another on the cornea and a relationship between the distance and the internal pressure.

3. The measurement system of claim 1, further comprising a refractometer that has an optical axis, the evaluation unit establishing a visual axis of the eye based on a position of the at least one Purkinje image and a relationship between the position of the at least one Purkinje image and the visual axis, and an adjustment unit connected to the refractometer to align the refractometer to the visual axis of the eye, whereby the measurement system further establishes refraction of the eye.

4. A system for adjusting an internal pressure of an eye during surgery, the system comprising
   the measurement system of claim 1,
   a rinsing fluid supply apparatus for supplying a rinsing fluid into the eye,
   an adjustment apparatus for adjusting a pressure of the supplied rinsing fluid, and
   a difference registering unit, connected to the evaluation device to receive the established internal pressure and to the adjustment apparatus to output a correcting variable and designed to establish a deviation of the received internal pressure from a target value and to calculate the correcting variable based on the established deviation.

* * * * *